United States Patent [19]
Katsuta et al.

[11] Patent Number: 5,866,598
[45] Date of Patent: Feb. 2, 1999

[54] MEDICAMENT FOR TREATING OR PREVENTING CEREBROVASCULAR DEMENTIA

[75] Inventors: Kiyotaka Katsuta; Hiroyuki Takamatsu; Yoshiko Ueda, all of Osaka; Hajime Nakanishi, Suita; Keizo Yoshida, Osaka, all of Japan

[73] Assignee: Fujisawa Pharmaceutical Co., Ltd., Osaka, Japan

[21] Appl. No.: 958,317

[22] Filed: Oct. 27, 1997

Related U.S. Application Data

[60] Continuation of Ser. No. 736,248, Oct. 24, 1996, Pat. No. 5,698,561, which is a division of Ser. No. 513,805, Sep. 8, 1995, Pat. No. 5,607,938.

[30] Foreign Application Priority Data

Mar. 8, 1993 [GB] United Kingdom ............ 9304701
Oct. 11, 1993 [GB] United Kingdom ............ 9320882
Feb. 16, 1994 [WO] WIPO ............ PCT/JP94/00249

[51] Int. Cl.$^6$ ............ A61K 31/44; A61K 31/415; A61K 31/40
[52] U.S. Cl. ............ 514/339; 514/396; 514/411
[58] Field of Search ............ 514/339, 396, 514/411

[56] References Cited

U.S. PATENT DOCUMENTS 4,845,115  7/1989  Tyers ............ 514/397

*Primary Examiner*—Kimberly Jordan
*Attorney, Agent, or Firm*—Oblon, Spivak, McClelland, Maier & Neustadt, P.C.

[57] ABSTRACT

Compounds for treating or preventing cerebrovascular diseases are disclosed. These compounds are 5-HT antagonists. More specifically, these compounds, when combined with pharmaceutically acceptable carriers or excipients and administered to animals including humans, are useful in treating or preventing cerebrovascular dementia.

2 Claims, No Drawings

MEDICAMENT FOR TREATING OR PREVENTING CEREBROVASCULAR DEMENTIA

This is a Continuation of application Ser. No. 08/736,248 filed Oct. 24, 1996, now U.S. Pat. No. 5,698,561, which is divisional of application Ser. No. 08/513,805, filed Sep. 8, 1995, now U.S. Pat. No. 5,607,938.

TECHNICAL FIELD

The present invention relates to a new use of a compound having 5-HT antagonism.

More particularly, the present invention relates to a new use of a compound having 5-HT antagonism (hereinafter referred to as "5-HT antagonist") such as $5\text{-HT}_1$ antagonism, $5\text{-HT}_2$ antagonism and $5\text{-HT}_3$ antagonism, especially $5\text{-HT}_3$ antagonism for treating or preventing cerebrovascular diseases.

Disclosure of the Invention

One object of the present invention is to provide a therapeutic or preventive agent of cerebrovascular diseases which comprises a 5-HT antagonist as an active ingredient.

Another object of the present invention is to provide a new use of a 5-HT antagonist as a therapeutic or preventive agent for cerebrovascular diseases.

Other object of the present invention is to provide a pharmaceutical composition for treating or preventing cerebrovascular diseases comprising a 5-HT antagonist, as an active ingredient, in association with a pharmaceutically acceptable, substantially non-toxic carrier or excipient.

Further object of the present invention is to provide a new use of a 5-HT antagonist for manufacturing a medicament for treating or preventing cerebrovascular diseases and conditions such as cerebral infarction, cerebrovascular dementia, and the like.

Still further object of the present invention is to provide a method for treating or preventing cerebrovascular diseases and conditions as mentioned above which comprises administering an effective amount of a 5-HT antagonist to a host such as animals, e.g. mammals including human.

It is known that 5-HT antagonists are of use for treating or preventing central nervous system (CNS) disorders such as psychosis (e.g. schizophrenia, mania, etc.), anxiety, and depression; pains or aches such as headaches (e.g. migraine, cluster headaches, vascular headaches, etc.), and neuralgia (e.g. trigeminal neuralgia, etc.); gastrointestinal disorders such as symptoms of gastrointestinal dysfunction such as occur with, for example, dyspepsia, peptic ulcer, reflux oesophagitis and flatulence, and irritable bowel syndrome (IBS); nausea or vomiting, each of which may be associated with cancer therapy; motion sickness; and the like.

The inventors of the present invention extensively investigated various effects of the 5-HT antagonists, and during such investigations, it has been found that the 5-HT antagonists are further of use for treating or preventing cerebrovascular diseases. This finding is really new and is not expectable at all for a person skilled in this field.

The 5-HT antagonist used in the present invention can be represented by the following general formulae:

(i) 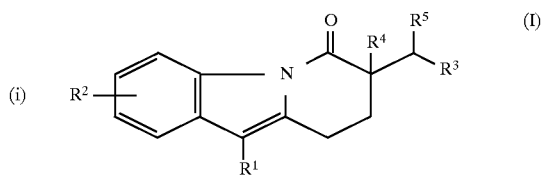

wherein
$R^1$ is hydrogen, lower alkyl, lower alkenyl or N,N-di(lower)alkylaminomethyl,
$R^2$ is hydrogen, lower alkyl or halogen,
$R^3$ is imidazolyl or pyridyl, each of which may have suitable substituent(s), and
$R^4$ is hydrogen, lower alkyl, lower alkenyl or hydroxy(lower)alkyl and
$R^5$ is hydrogen, hydroxy or acyloxy, or
$R^4$ and $R^5$ are linked together to form an additional bond, or a pharmaceutically acceptable salt thereof, (ii) 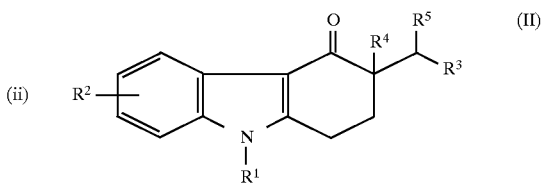

wherein $R^1$, $R^2$, $R^3$, $R^4$ and $R^5$ are each as defined above, or a pharmaceutically acceptable salt thereof, and (iii) 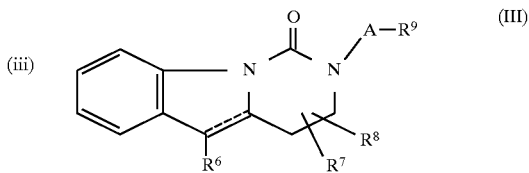

wherein $R^6$, $R^7$ and $R^8$ are each hydrogen, lower alkyl, lower alkenyl, aryl or ar(lower)alkyl,
$R^9$ is imidazolyl which may have suitable substituent(s) or pyridyl,
A is lower alkylene, and - - - is single bond or double bond,
or a pharmaceutically acceptable salt thereof.

In the compounds of the formulae (I), (II) and (III), a suitable pharmaceutically acceptable salt of these compounds includes conventional one such as acid addition salt with an organic or inorganic acid (e.g. hydrochloride, sulfate, formate, acetate, etc.), or a salt with a base such as alkali metal salt (e.g. sodium salt, potassium salt, etc.), alkaline earth metal salt (e.g. calcium salt, etc.), organic basic salt (e.g. cyclohexylamine salt, etc.), and the like.

The most preferred embodiment of the 5-HT antagonist used in the present invention is as follows.

8,9-Dihydro-10-methyl-7-[(5-methyl-1H-imidazol-4-yl)methyl]pyrido[1,2-a]indol-6(7H)-one or its hydrochloride salt;

1,2,3,9-Tetrahydro-9-methyl-3-[(2-methyl-1H-imidazol-1-yl)methyl]-4H-carbazol-4-one or its hydrochloride and/or its hydrate; and 3,4-Dihydro-5-methyl-2-[1-(5-methyl-1H-imidazol-4-yl)ethyl]pyrimido[1,6-a]indol-1(2H)-one or its hydrochloride.

The compounds of the general formulae (I), (II) and (III), and the specific compounds mentioned above are known compounds, and the methods for preparation thereof are described, for example, in the following publications, or they can be prepared by a conventional method.

European Patent Publication 0361317A
European Patent Publication 0191562A
European Patent Publication 0420086A The suitable examples and illustrations of the various definitions used in the compounds of the formulae (I), (II) and (III) are explained in detail in the following.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, t-butyl, pentyl, hexyl, preferably one having 1 to 4 carbon atoms, and the like, in which the most preferred one is methyl, ethyl or propyl.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is allyl.

Suitable "hydroxy(lower)alkyl" is lower alkyl as mentioned above which is substituted by hydroxy and may include hydroxymethyl, hydroxyethyl, hydroxypropyl, and the like, in which the most preferred one is hydroxymethyl.

Suitable "halogen" means fluoro, chloro, bromo and iodo, in which the most preferred one is chloro.

Suitable "imidazolyl" means 1H-imidazol-1-yl, 1H-imidazol-2-yl, 1H-imidazol-4-yl and 1H-imidazol-5-yl.

Suitable "pyridyl" means 2-pyridyl, 3-pyridyl and 4-pyridyl.

Suitable substituent in the terms "imidazolyl or pyridyl, each of which may have suitable substituent(s)" is conventional one used in a pharmaceutical field and may include lower alkyl as mentioned above, imino-protective group as mentioned below, and the like.

Suitable acyl moiety in the term "acyloxy" may include conventional one derived, for example, from carboxylic, carbonic, sulfonic and carbamic acids, and the preferable example thereof is lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), and the like, in which the most preferred one is acetyl.

These acyl group may be substituted with suitable substituent(s) such as halogen (e.g. chlorine, bromine, iodine, fluorine).

Suitable "imino-protective group" may include conventional one, and the preferable example thereof is ar(lower) alkyl such as mono-(or di- or tri-)phenyl(lower)alkyl (e.g. benzyl, benzhydryl, trityl, etc.), acyl such as N,N-di(lower) alkylsulfamoyl (e.g. N,N-dimethylsulfamoyl, etc.), lower alkanesulfonyl (e.g. mesyl, etc.), arenesulfonyl (e.g. tosyl, etc.), and the like, in which the most preferred one is trityl, benzyl or N,N-dimethylsulfamoyl.

Suitable "N,N-di(lower)alkylaminomethyl" may include N,N-dimethylaminomethyl, and the like.

Suitable "aryl" may include phenyl, tolyl, xylyl, mesityl, cumenyl, naphthyl, and the like, in which the preferred one is $C_6-C_{10}$ aryl and the most preferred one is phenyl.

Suitable "ar(lower)alkyl" may include mono-(or di- or tri-)phenyl(lower)alkyl such as trityl, benzhydryl, benzyl, phenethyl, and the like, in which the preferred one is $C_6-C_{10}$ ar($C_1-C_6$)alkyl and the most preferred one is benzyl.

Suitable "lower alkylene" may include straight or branched one, having 1 to 6 carbon atom(s), such as methylene, methylmethylene, ethylene, trimethylene, propylene, tetramethylene, and the like, in which the most preferred one is methylmethylene.

Particularly, the preferred embodiments of $R^1$, $R^2$ $R^3$, $R^4$, $R^5$, $R^6$, $R^7$, $R^8$, $R^9$, A and - - - are as follows.

$R^1$ is hydrogen; lower alkyl such as methyl, ethyl, propyl, etc.; lower alkenyl such as allyl, etc.; or N,N-di(lower) alkylaminomethyl such as N,N-dimethyl aminomethyl, etc.;

$R^2$ is hydrogen; lower alkyl such as methyl, etc.; or halogen such as chloro;

$R^3$ is 1H-imidazolyl which may have one or more, preferably one to three substituent(s) selected from lower alkyl and imino-protective group such as 2-lower alkyl-1H-imidazol-1-yl (e.g. 2-methyl-1H-imidazol-1-yl, etc.), 1H-imidazol-2-yl, 1-ar(lower)alkyl-1H-imidazol-2-yl (e.g. 1-trityl-1H-imidazol-2-yl, etc.) 1-ar(lower)alkyl-5-lower alkyl-1H-imidazol-4-yl (e.g. 5-methyl-1-trityl-1H-imidazol-4-yl, 1-benzyl-5-methyl-1H-imidazol-4-yl, etc.), 5-lower alkyl-1H-imidazol-4-yl (e.g. 5-methyl-1H-imidazol-4-yl, etc.), 1-ar(lower)alkyl-1H-imidazol-4-yl (e.g. 1-trityl-1H-imidazol-4-yl, etc.), 1H-imidazol-4-yl, 2-lower alkyl-5-lower alkyl-1H-imidazol-4-yl (e.g. 2,5-dimethyl-1H-imidazol-4-yl, etc.), 1-ar(lower)alkyl-2-lower alkyl-1H-imidazol-4-yl (e.g. 2-methyl-1-trityl-imidazol-4-yl, etc.), 2-lower alkyl-1H-imidazol-4-yl (e.g. 2-methyl-1H-imidazol-4-yl, etc.), 1-lower alkyl-1H-imidazol-4-yl (e.g. 1-methyl-1H-imidazol-4-yl, etc.), 1-lower alkyl-5-lower alkyl-1H-imidazol-4-yl (e.g. 1,5-dimethyl-1H-imidazol-4-yl, etc.) and 1-di(lower)alkylaminosulfonyl-5-lower alkyl-1H-imidazol-4-yl (e.g. 1-dimethylaminosulfonyl-5-methyl-1H-imidazol-4-yl, etc.), 1-lower alkyl-1H-imidazol-5-yl (e.g. 1-methyl-1H-imidazol-5-yl, etc.) and 1-lower alkyl-4-lower alkyl-1H-imidazol-5-yl (e.g. 1,4-dimethyl-1H-imidazol-5-yl, etc.); pyridyl which may have lower alkyl such as 3-pyridyl which may have suitable substituent(s) such as 3-pyridyl and 2-lower alkyl-3-pyridyl (e.g. 2-methyl-3-pyridyl, etc.);

$R^4$ is hydrogen; lower alkyl such as methyl, ethyl, propyl, etc.; lower alkenyl such as allyl, etc.; or hydroxy(lower) alkyl such as hydroxymethyl, etc.; and $R^5$ is hydrogen; hydroxy; or acyloxy such as lower alkanoyloxy (e.g. acetoxy, etc.), and the like; or $R^4$ and $R^5$ are linked together to form an additional bond;

$R^6$ is hydrogen; lower alkyl (e.g. methyl, ethyl, isopropyl, etc.); lower alkenyl (e.g. allyl, etc.); aryl (e.g. phenyl, etc.); or ar(lower)alkyl such as mono- or di- or triphenyl(lower) alkyl (e.g. benzyl, etc.);

$R^7$ is hydrogen; or lower alkyl (e.g. methyl, etc.);

$R^8$ is hydrogen; or lower alkyl (e.g. methyl, etc.);

$R^9$ is imidazolyl which may have one to three substituent (s) selected from the group consisting of lower alkyl and imino-protective group, for example, 1H-imidazol-4-yl, 5-lower alkyl-1H-imidazol-4-yl (e.g. 5-methyl-1H-imidazol-4-yl, 5-ethyl-1H-imidazol-4-yl, etc.), 1-ar(lower) alkyl-5-lower alkyl-1H-imidazol-4-yl such as 1- mono- or di- or triphenyl(lower)alkyl-5-lower alkyl-1H-imidazol-4-yl (e.g. 1-trityl-5-methyl-1H-imidazol-4-yl, 1-trityl-5-ethyl-1H-imidazol-4-yl, etc.), 1-ar(lower)alkyl-1H-imidazol-4-yl such as 1- mono- or di- or triphenyl(lower)alkyl-1H-imidazol-4-yl (e.g. 1-trityl-1H-imidazol-4-yl, etc.), 1-lower alkyl-5-lower alkyl-1H-imidazol-4-yl (e.g. 1-methyl-5-methyl-1H-imidazol-4-yl, etc.); pyridyl (e.g. 4-pyridyl, etc.);

A is lower alkylene (e.g. methylene, methylmethylene, ethylmethylene, etc.); and - - - is single bond or double bond.

For therapeutic or preventive administration, the agent of the present invention are used in the form of conventional pharmaceutical preparation which contains the 5-HT antagonist, as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, and the like.

If needed, there may be included in the above preparation auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the 5-HT antagonist may vary from and also depend upon the age, conditions of the patient, a kind of diseases, a kind of the 5-HT antagonist to be applied, and the like. In general, amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg, 200 mg, or 300 mg of the 5-HT antagonist may be used in the body.

In order to show the usefulness of the present inventions, the following examples are given.

TEST METHOD

The experiment was carried out using male Sprague Dawley rats (272–345 g). The animals were anesthetized with 2% halothane in a mixture of 70% nitrous oxide and a balance of oxygen delivered through a close fitting face mask. The animals were placed in the lateral position, and a 2 cm skin incision was made at the midpoint between the left orbit and the external auditory canal without removing the zygomatic arch. The temporal muscle was divided midway vertically and reflected forward and downward with a retractor. The inferotemporal fossa was exposed under a surgical microscope, and a small craniectomy was made using a dental drill. The proximal portion of the middle cerebral artery was permanently electrocoagulated with bipolar forceps and was cut to ensure the completeness of the vascular occlusion. The skin was sutured, and the animals were returned to their cages.

Twenty four hours after ischemia, the animals were anesthetized with thiopental-Na (50 mg/kg, i.p.) and then sacrificed by intracardiac perfusion with 200 ml of heparinized saline. The brain was cut into 6 coronal slices (2 mm thick), the brain slices were stained with 2% (W/V) triphenyltetrazolium chloride in saline at 37° C. The areas of ischemic damage were delineated at 6 preselected coronal levels from anterior 3.75 mm to arterior 13.5 mm, and the extent of ischemic damage were determined from these photographs using a digitizer. The ischemic damage was expressed as % of total infarction areas. The drugs were injected intravenously via tail vein immediately after surgery.

The statistical analyses of data were carried out using Dunnett's test.

Test Compounds (+)-8,9-Dihydro-10-methyl-7-[(5-methyl-1H-imidazol-4-yl)methyl]pyrido[1,2-a]indol-6(7H)-one hydrochloride [hereinafter referred to as Compound A]

1,2,3,9-Tetrahydro-9-methyl-3-[(2-methyl-1H-imidazol-1-yl)methyl]-4H-carbazol-4-one hydrochloride dihydrate [hereinafter referred to as Compound B]

(+)-3,4-Dihydro-5-methyl-2-[1-(5-methyl-1H-imidazol-4-yl)ethyl]pyrimido[1,6-a]indol-1(2H)-one hydrochloride [hereinafter referred to as Compound C]

Test Result

TABLE

Effects of 5-HT antagonists on ischemic damage by focal brain ischemia

| drug | dose (mg/kg, i.v.) | n | % of infarction area (Mean ± S.E.) |
|---|---|---|---|
| control | 0 (saline) | 8 | 21.74 ± 1.49 |
| Compound A | 0.001 | 8 | 19.02 ± 1.37 |
|  | 0.01 | 8 | 18.51 ± 0.89 |
|  | 0.1 | 8 | 16.97 ± 1.12* |
| control | 0 (saline) | 8 | 16.65 ± 0.82 |
| Compound B | 1.0 | 8 | 14.78 ± 1.39 |
|  | 10.0 | 8 | 11.40 ± 0.48** |
| control | 0 (saline) | 8 | 18.65 ± 0.76 |
| Compound C | 0.01 | 7 | 16.09 ± 1.12 |
|  | 0.1 | 8 | 14.12 ± 1.46* |
|  | 1.0 | 7 | 13.13 ± 1.13* |

*: P < 0.05 vs control
**: P < 0.01

As evident from the Test Results, the 5-HT antagonists showed decrease of cerebral infarction area, and therefore are of much use for treating and preventing cerebrovascular diseases.

We claim:

1. A method for treating or preventing cerebrovascular dementia, comprising administering to a mammal in need thereof an effective amount of a compound of the formula:

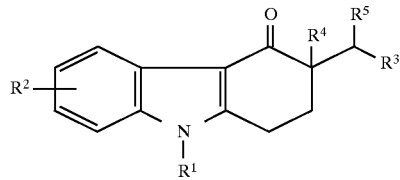

wherein $R^1$ is hydrogen, lower alkyl, lower alkenyl, or N,N-di(lower)alkylaminomethyl;

$R^2$ is hydrogen, lower alkyl, or halogen;

$R^3$ is imidazolyl or pyridyl, each of which may have suitable substituent(s), and the imidazolyl is bonded to the remainder of the molecule at the atom at position 2, 4, or 5 of the imidazolyl; and $R^4$ is hydrogen, lower alkyl, lower alkenyl, or hydroxy (lower)alkyl, and $R^5$ is hydrogen, hydroxy, or acyloxy, or $R^4$ and $R^5$ are linked together to form an additional bond;

or a pharmaceutically acceptable salt thereof.

2. A pharmaceutical composition for treating or preventing cerebrovascular disease, comprising a compound of the formula:

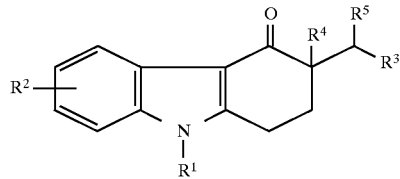

wherein $R^1$ is hydrogen, lower alkyl, lower alkenyl, or N,N-di(lower)alkylaminomethyl;

$R^2$ is hydrogen, lower alkyl, or halogen;

$R^3$ is imidazolyl or pyridyl, each of which may have suitable substituent(s), and the imidazolyl is bonded to the remainder of the molecule at the atom at position 2, 4, or 5 of the imidazolyl; and $R^4$ is hydrogen, lower alkyl, lower alkenyl, or hydroxy (lower)alkyl, and $R^5$ is hydrogen, hydroxy, or acyloxy, or $R^4$ and $R^5$ are linked together to form an additional bond;

or a pharmaceutically acceptable salt thereof.

* * * * *